United States Patent [19]

Shinkai et al.

[11] 4,171,440
[45] Oct. 16, 1979

[54] PROCESS FOR PURIFICATION OF 9-(2,6-DIHALOBENZYL)ADENINES

[75] Inventors: Ichiro Shinkai, Westfield; Leonard M. Weinstock, Belle Mead; Roger J. Tull, Metuchen, all of N.J.

[73] Assignee: Merck & Co., Inc., Rayway, N.J.

[21] Appl. No.: 916,378

[22] Filed: Jun. 16, 1978

Related U.S. Application Data

[63] Continuation of Ser. No. 843,919, Oct. 20, 1977, abandoned.

[51] Int. Cl.² .......................................... C07D 473/40
[52] U.S. Cl. .................................................. 544/277
[58] Field of Search ................................ 544/276, 277

[56] References Cited

U.S. PATENT DOCUMENTS

| 3,846,426 | 11/1974 | Lira et al. | 424/253 |
| 3,930,005 | 12/1975 | Wojnar et al. | 544/276 |

*Primary Examiner*—Nicholas S. Rizzo
*Attorney, Agent, or Firm*—Walter Patton; Harry E. Westlake, Jr.

[57] ABSTRACT

An efficient method has been found for the removal of the 3-isomer present in crude 9-(2-chloro-6-fluorobenzyl)adenine. Crude 9-(2-chloro-6-fluorobenzyl)adenine is transalkylated in sulfuric acid-toluene to reduce the 3-isomer to undetectable levels (<100 ppm). Alternately, crude 9-(3-chloro-6-fluorobenzyl)adenine is first treated with dilute nitric acid to remove the bulk of the 3-isomer followed by transalkylation to sulfuric acid-toluene to reduce the 3-isomer to undetectable levels (<100 ppm). The overall yield for this purification is about 95% based on the 9-(2-chloro-6-fluorobenzyl)adenine content of the crude material. The resulting pure 9-(2-chloro-6-fluorobenzyl)adenine has anticoccidial activity and is useful in controlling cecal and/or intestinal coccidiosis when administered in minor quantities to animals, in particular to poultry usually in admixture with animal sustenance.

7 Claims, No Drawings

PROCESS FOR PURIFICATION OF 9-(2,6-DIHALOBENZYL)ADENINES

This is a continuation of copending application U.S. Ser. No. 843,919, filed Oct. 20, 1977 abandoned.

BACKGROUND OF THE INVENTION

This invention relates to a novel process for obtaining pure 9-(2,6-dihalobenzyl)adenines from crude reaction mixtures containing substantial amounts of 3-(2,6-dihalobenzyl)adenines. Said crude reaction mixtures containing 9-(2,6-dihalobenzyl)adenines can be obtained by alkylating adenine by the process described in U.S. Ser. No. 766,326 filed Feb. 7, 1977 or U.S. Pat. No. 3,846,426. Said alkylated adenines are described in U.S. Pat. No. 3,846,426 as being useful in the treatment and prevention of coccidiosis.

Coccidiosis is a widespread poultry disease which is produced by infections of protozoa of the genus Eimeria which causes severe disorders in the intestines and ceca of poultry. Some of the most significant of these species are *E. tenella, E. acervulina, E. necatrix, E. brunetti* and *E. maxima*. This disease is generally spread by the birds picking up the infectious organism in droppings on contaminated litter or ground, or by way of contaminated food or drinking water. The disease is manifested by hemorrhage, accumulation of blood in the ceca, passage of blood in the droppings, weakness and digestive disturbances. The disease often terminates in the death of the animals, but the flow which survive severe infections have had their market value substantially reduced as a result of the infection. Coccidiosis is, therefore, a disease of great economic importance and extensive work has been done to find new and improved methods for controlling and treating coccidial infections in poultry.

9-(2,6-Dihalobenzyl)adenines, useful for the control and treatment of coccidial infections, are prepared by alkylation of adenine. Alkylation of adenine results primarily at the 9-position, but substantial amounts of the undesired 3-isomer and traces of the 7-isomer are also formed. The alkylation reaction and the structure of the main products i.e., the 3-isomer and 9-isomer are illustrated by the following equation:

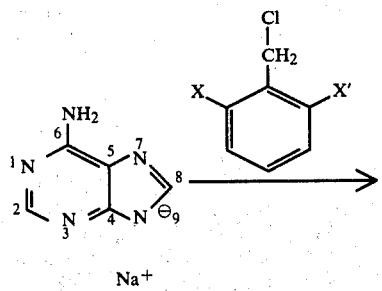

-continued

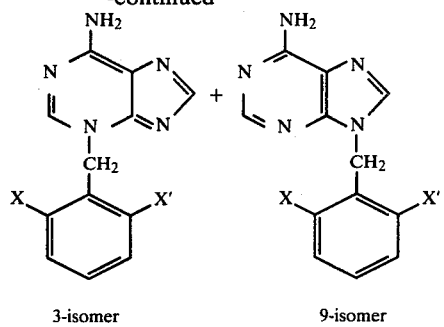

3-isomer      9-isomer wherein X and X' are independently fluorine, chlorine or bromine.

After the reactants, adenine and α-chloro-2,6-dihalotoluene, are contacted with each other in the reaction medium, the product of the reaction, i.e., the 9-(dihalobenzyl)adenine, along with the other isomers that form, (e.g. the 3-isomer and to a lesser extent the 7-isomer) will either remain entirely in solution or precipitate on standing, depending upon the quantity of solvent utilized. Upon completion of the reaction, the reaction mixture may be cooled, e.g., to a temperature of about room temperature to precipitate a solid product or to precipitate a further quantity of this product. The product is then isolated in the usual manner, such as by filtration, and, if desired, purified by conventional methods such as washing with ethanol or water and recrystallizing from a suitable solvent such as acetic acid, aqueous acetic acid, dimethylformamide or dimethylsulfoxide. Swishing the product with dilute nitric acid or tetrafluoroboric acid ($HBF_4$) also results in some purification.

The conventional purification methods recited above such as acetic acid recrystallization of crude 9-(2,6-dihalobenzyl)adenine produces a 99% pure product containing about 1% of the 3-isomer. Since it was learned that the 3-isomer gives a weak positive Ames test, an objective was set aimed at its virtual complete removal to levels less than 100 ppm. The process of the present invention is directed to methods for 3-isomer removal which involves a transalkylation reaction wherein the 2,6-dihalobenzyl group at the 3-position of adenine is removed as a carbenium ion by sulfuric acid and the carbenium ion allowed to react with a suitable carbenium ion trap. Alternatively, the crude 9-(2,6-dihalobenzyl)adenine may be subjected to a first step preliminary purification by extraction with dilute mineral acid before treatment with sulfuric acid as a second step. Furthermore, any conventional purification method recited above may be used as a preliminary first step to obtain partial purification before treatment with sulfuric acid. The sulfuric acid treatment process of the present invention produces 9-(2,6-dihalobenzyl)adenine containing <100 ppm of 3-isomer in 92–94% yield over the two steps or in 96% yield in one step.

SUMMARY OF THE INVENTION

The teachings set forth herein with respect to 9-(2-chloro-6-fluorobenzyl)adenine are generally equally applicable to 9-(2,6-dihalobenzyl)adenines.

There are two chemical differences between the 9-isomer and the 3-isomer which form the basis for the purification of the present invention: (1) the 3-isomer ($pK_a$ 5.6) is 40 times more basic than 9-(2-chloro-6- fluorobenzyl)adenine (p$K_a$ 4.0) and (2) the 3-isomer is chemically less stable than 9-(2-chloro-6-fluorobenzyl)adenine in strong acid solutions.

Advantage is taken of the p$K_a$ difference to effect substantial reduction of the 3-isomer in the crude reaction mixture by simply extracting the solid crude with dilute mineral acid solution. Thus extraction of crude 9-(2-chloro-6-fluorobenzyl)adenine containing 20% of the 3-isomer with a dilute aqueous solution of nitric acid produces 9-(2-chloro-6-fluorobenzyl)adenine containing 3–4% of the 3-isomer with a 96–97% recovery of 9-(2-chloro-6-fluorobenzyladenine. Repeating this procedure on the enriched 9-(2-chloro-6-fluorobenzyl)adenine sample fails to reduce the 3-isomer level below about 0.3–0.5% (3000–5000 ppm). This is due to the pronounced tendency toward solid solutions involving the 9-isomer and 3-isomer. The same problem is encountered when 3-isomer removal is attempted using two acetic acid recrystallizations. The 3-isomer level reaches the range of 0.05–0.1% (500–1000 ppm) even though the liquid phase is not saturated in the 3-isomer.

Very low levels of the 3-isomer (<100 ppm) have been achieved by the process of the present invention by selective chemical degradation of the 3-isomer, taking advantage of its inherent lower thermodynamic stability. The 3-isomer can be totally degraded to adenine and a benzyl polymer by treatment with 96% sulfuric acid without affecting the 9-isomer according to the following equation:

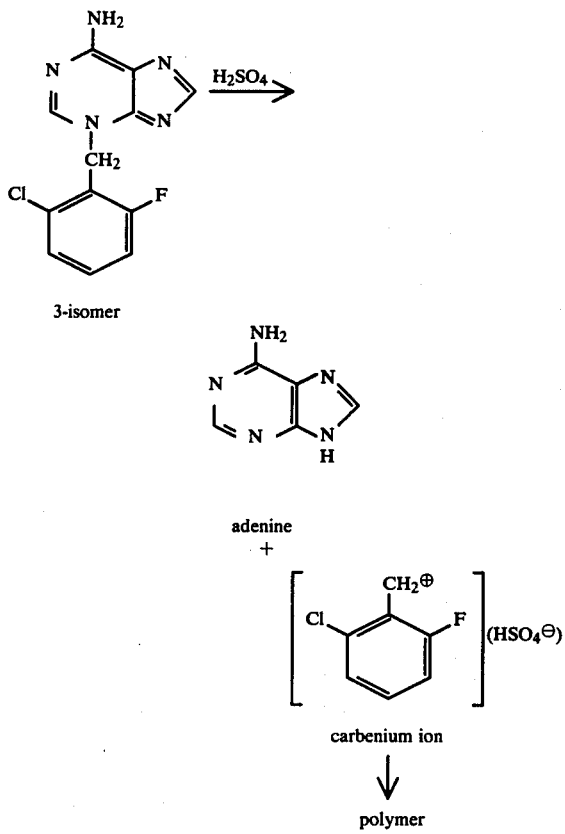

Under the same conditions 9-(2-chloro-6-fluorobenzyl)adenine is unreactive. Thus, treatment of 9-(2-chloro-6-fluorobenzyl)adenine containing 3–4% of 3-isomer with 96% sulfuric acid results in a 96% recovery of 9-(2-chloro-6-fluorobenzyl)adenine containing <100 ppm of the 3-isomer. It has proved very difficult to completely separate the polymer from the 9-(2-chloro-6-fluorobenzyl)adenine. This problem has been overcome by the process of the present invention by carrying out the sulfuric acid treatment in the presence of a suitable carbenium ion trap.

Suitable carbenium ion traps are those well known in the art such as dialkyl sulfide, wherein the alkyl group contains 1 to 5 carbon atoms; diaryl sulfide, wherein the aryl groups contain 6 to 18 carbon atoms; benzene, toluene, xylene, mixed xylenes, mesitylene, alkoxybenzene wherein the alkyl group contains 1 to 3 carbon atoms such as anisole; thiophene, iodobenzene, naphthalene or triphenylphosphine. Out of several substances examined, toluene and mixed xylenes were found to be the most suitable for this purpose. Toluene reacts rapidly with the intermediate carbenium ion to form the transalkylation product, according to the following equation:

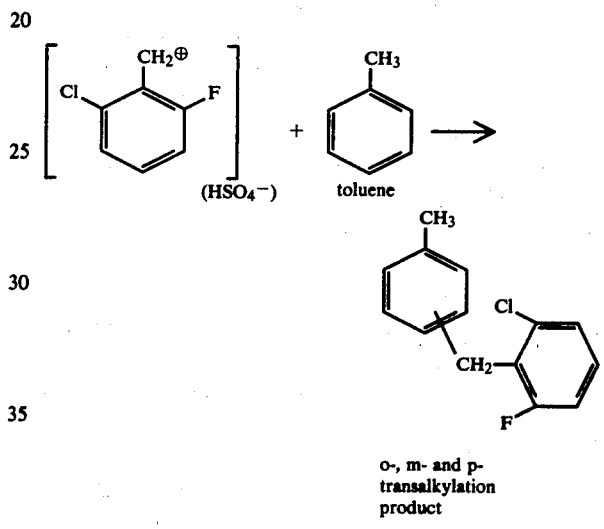

o-, m- and p-transalkylation product thus preventing the polymerization. Utilizing the method of sulfuric acid transalkylation in the presence of toluene, 9-(2-chloro-6-fluorobenzyl)adenine containing 3–4% of 3-isomer provides high purity 9-(2-chloro-6-fluorobenzyl)adenine containing no polymer and <100 ppm of the 3-isomer in 97–98% yield.

Crude 9-(2-chloro-6-fluorobenzyl)adenine containing 3-isomer in the range of 20% may be extracted with a solution of dilute mineral acid to achieve a partial removal of the undesired 3-isomer and particularly to remove traces of the 7-isomer, if desired, prior to treatment with sulfuric acid.

The mineral acid used is not critical provided it does not react with the 9-isomer. Suitable mineral acids are hydrochloric, phosphoric or nitric acid. Nitric acid is preferred. To avoid excessive loss of the 9-isomer during the extraction, best results are obtained if the quantity of the 3-isomer is determined by L.C. assay and an equimolar (or a slight excess) of acid with respect to 3-isomer is added. The extraction may be carried out between room temperature and about 100° C. The preferred conditions are reflux temperature with vigorous stirring. Extraction with vigorous stirring for about 1 hour to about 5 hours is sufficient. An optimal time is about 2 hours. The hot mixture is collected by filtration and washed with hot water, with base to remove excess acid and finally with hot water again. The resulting partially purified material enriched in the 9-isomer is subjected to treatment with sulfuric acid in the presence of a carbenium trap to obtain pure 9-(2-chloro-6-fluorobenzyl)adenine.

According to the preferred process of the present invention, crude 9-(2-chloro-6-fluorobenzyl)adenine is treated with concentrated sulfuric acid (96% assay) to selectively dealkylate the 3-isomer and regenerate adenine. At least a twice molar excess of sulfuric acid with respect to the 3-isomer are required for the dealkylation. The concentration of the 3-isomer is determined by liquid chromatography assay (L.C. assay) as described below under the heading Assay. The amount of excess sulfuric acid used is not critical. For example, an equal weight of crude 9-(2-chloro-6-fluorobenzyl)adenine to volume of sulfuric acid or up to 10× volume sulfuric acid with respect to weight of crude 9-(2-chloro-6-fluorobenzyl)adenine may be used. A preferred ratio is 1 g. of crude 9-(2-chloro-6-fluorobenzyl)adenine for each 2 ml. of sulfuric acid.

The quantity of carbenium ion trap used is not critical, provided there is at least an equimolar amount with respect to the 3-isomer. However, a large excess is preferred because it acts as both a reagent and a solvent.

The crude 9-(2-chloro-6-fluorobenzyl)adenine is treated with concentrated sulfuric acid at a temperature range of from room temperature to about 90° C. A preferred temperature is room temperature with an approximately 10 minute final heating period at about 80° C. to insure complete reaction. The reaction time is not critical provided a minimum of 2 hours has elapsed. After the initial 2 hours, the reaction is essentially complete and may be terminated when convenient. No deleterious effects are observed even if the reaction is allowed to proceed for 36 hours. A convenient optimal time is about 5 hours.

The aqueous layer is separated from the reaction. Warming may be necessary up to a temperature of 50° C. to 100° C. depending on the amount of solvent and acid present to facilitate the separation of the aqueous phase. The aqueous phase is made basic by the addition of base. Any base is suitable provided only that it forms a water soluble sulfate. Suitable bases are sodium hydroxide, potassium hydroxide, ammonium hydroxide, sodium carbonate, and potassium carbonate. The preferred base is sodium hydroxide. After the aqueous phase is made strongly basic the pure product precipitates and is collected by filtration and washed with water or an aqueous alcohol solution and dried in vacuo.

An added advantage of the present process is that the costly adenine can be recovered from the alkaline filtrate by neutralizing the filtrate and collecting the precipitated adenine by filtration.

ASSAY

A. Assay for weight % of 9-isomer and for 3-isomer when 3-isomer is present in excess of 1%

The weight % of 9-isomer, 3-isomer and 7-isomer in the product is determined by high pressure liquid chromatography (L.C.) and U.V., respectively. The weight % of 9-isomer is determined by a high pressure liquid chromatography assay (L.C.) using a 15 cm., 5 micron totally porous silica column (DuPont, Zorbax-SIL) eluted with $CHCl_3$:MeOH (95:5) and measuring the absorbance of each component at 254 nm, 9-benzyladenine was used as an internal standard (accurate to ±0.3%). The weight % of the 3-isomer is determined by U.V. assay. The sample is assayed in 0.1N methanolic base at 310 nm, the 3-isomer has an $\epsilon$ of 2300 at this wave-length and the 9-isomer does not absorb (accurate to ±0.1%).

B. Assay for weight % of trace amounts of 3-isomer after sulfuric acid treatment The weight % of 3-isomer in the product is determined by high pressure liquid chromatography (L.C.) using a 10 micron, 30 cm., microporous, octadecylsilane bonded phase column (Waters' Associates Micro Bondapak C-18 No. 27324) with a methanol, aqueous phosphate mobile phase at 35° C. The mobile phase is prepared from 30 parts methanol plus 70 parts 0.01M $Na_2HPO_4$ adjusted to pH 7 with $H_3PO_4$. Detection is by U.V. at 280 nm. The limit of detection is 100 ppm.

The following non-limiting Examples will serve to further illustrate the instant invention.

EXAMPLE 1

Process for Alkylating Adenine with α,2-Dichloro-6-fluorotoluene in the Presence of Aliquat 336 in Acetone (Solid-liquid Reaction Mixture)

Step A—Alkylation

A 250ml. round bottom flask was sequentially charged with 100 ml. of acetone, 6.95 g. of adenine (97% pure, 50 mmole) and 4.0 g. of sodium hydroxide solution (assay 50%, 50 mmole) and the suspension refluxed for one and one-half hours. The suspension was charged with a solution of 9.8 g. of α,2-dichloro-6-fluorotoluene (91.4% pure, 50 mmole) and 1.25 g. of Aliquat 336 (Aliquat 336 is a mixture of tetraalkylammonium salts in which the alkyl groups are primarily caprylyl ($C_8$), manufactured by General Mills, Inc., Chemical Division, 4320 West 77th Street, Minneapolis, Minn.) (2.5 mmole, 5 mole %) in 10 ml. of acetone and refluxed, with rapid stirring, for six hours. (In the absence of the "phase transfer catalyst", Aliquat 336, the reaction is about 5× slower). The reaction mixture was cooled to room temperature and the solids collected by filtration. The solids were washed twice with 15 ml. of acetone and then swished with 50 ml. of 0.1N sodium hydroxide solution for 15 minutes (this removes any unreacted adenine and the NaCl formed during the alkylation). The solids were collected by filtration, washed twice with 20 ml. of water and dried in vacuo (100° C. for 4.5 hours) to give 13.12 g. of 2-chloro-6-fluorobenzylated adenines (94.4%). U.V. (N/10 HCl)λmax=262, E%=534; L.C. wt. % 9-isomer=77.4; U.V. wt. % 3-isomer=20.4.

STEP B—Purification

Ten g. of the above material was added to 18 ml. of hot glacial acetic acid (~60° C.). The mixture was heated to 110° C. (solution occurred between 60° and 90° C.), filtered and the filtrate added to 80 ml. of hot water (95° C.) over a five minute period with rapid stirring (2 more ml. of acetic acid were used for rinses). When the temperature dropped to 37° C. the suspended solids were collected by filtration, washed once with 10 ml. of 4:1 $H_2O$:HOAc and twice with 15 ml. of water. Vacuum oven drying (100° C. for 6 hours) gave 7.64 g. of 9-(2-chloro-6-fluorobenzyl)adenine, 76.4%. U.V. (N/10 HCl)~max=260, E% 570; DSC=0.5 mole % impurity, m.p. (uncor)=244.5°–246° C.; tlc on silic gel in $CHCl_3$: MeOH (10:1) showed one minor impurity at $R_f$=0.57 and a main spot at $R_f$=0.86.

EXAMPLE 2

One Step Purification of Crude 9-(2-Chloro-6-fluorobenzyl)adenine by Treatment with Sulfuric Acid To a stirred suspension of crude 2-chloro-6-fluorobenzylated adenines (2.0 g., L.C. assay wt.% of 9-/3-/7-isomer=79.7/17.8/1.2) in xylene (4 ml.) was added dropwise concentrated sulfuric acid (96%, 4 ml.) at room temperature. The mixture was stirred for 12 hours at room temperature and then for an additional 10 minutes at 80° C. After the reaction mixture was cooled to room temperature, the mixture was poured into ice water (25 ml.) containing xylene (10 ml.). The resulting mixture was transferred to a steam-jacketed separatory funnel and heated to 85° C. in order to redissolve the pecipitate. The aqueous layer was separated and made basic by addition of concentrated ammonium hydroxide. The precipitated solids were filtered and washed with hot water (2×10 ml.). Yield, 1.53 g. (95.6% based on available 9-isomer). L.C. assay 9-isomer 100.07%; 3-isomer, none detectable (<100 ppm); 7-isomer ~0.8%.

EXAMPLE 3

Two Step Purification of Crude 9-(2-Chloro-6-fluorobenzyl)adenine by Extraction with Dilute Nitric Acid and Treatment with Sulfuric Acid

Step A.—Extraction with Dilute Nitric Acid

A suspension of 40.0 g (0.144 mole) crude 2-chloro-6-fluorobenzylated adenines (wt. % of 9-3-isomers=79.1/19.3 determined by L.C. assay) representing 31.64 g. of 9-isomer and 7.72 g. of 3-isomer in 440 ml. water containing 19.0 ml. (0.0285 mole) of 1.5N nitric acid was heated under reflux for 2 hours with vigorous stirring. The mixture was filtered while hot onto a pre-heated funnel, washed with hot water (3×50 ml. slurries), conc. NH$_4$OH (2×25 ml.) and hot water (3×50 ml.). The product was sucked damp-dry and finally dried in vacuo at 65°-70° C. overnight to yield 31.67 g. (97.1% yield) of 9-isomer enriched 2-chloro-6-fluorobenzylated adenines. This yield is based on available 9-isomer and is corrected for purity. L.C. assay 9-isomer 97.2% and 3-isomer 3.0%.

Step B.—Dealkylation of 3-(2-Chloro-6-fluorobenzyl)adenine with Sulfuric Acid To a vigorously stirred suspension of 50.0 g. (0.18 mole) of 9-isomer enriched 2-chloro-6-fluorobenzylated adenines (wt. % of 9-/3-isomers=96.8/3.2 by L.C. assay) representing 48.4 g. of 9-isomer and 1.6 g. of 3-isomer in 100 ml. of toluene (reagent grade) was added dropwise 100 ml. of concentrated sulfuric acid (assay=96.02%) with ice/water cooling as required to maintain a temperature of 50°-60° C. The mixture was heated with stirring at 50°-60° C. for 18 hours (all the solid dissolved in the acid to give a two-phase system). The batch was cooled to room temperature and poured into ice/water (300 ml.) whereupon the product precipitated as the sulfate salt. The mixture was transferred to a steam-jacketed separatory funnel using hot water rinses and heated to 80°-85° C. in order to redissolve the precipitate and effect separation of the aqueous layer from the toluene layer. The aqueous layer (650 ml.) was separated and washed with 50 ml. of hot toluene using the same apparatus. The aqueous layer (while still warm) was made basic (pH 10) by the cautious addition of concentrated ammonium hydroxide solution. The precipitated white solid was aged with stirring for 1 hour and collected while the batch was still warm. The product was washed with hot water (3×100 ml.) and 50% aqueous methanol (2×100 ml.). The batch was sucked damp-dry and finally dried in vacuo at 70° C. overnight to give pure 9-(2-chloro-6-fluorobenzyl)adenine. The yield was 47.8 g. (98.8% based on available 9-isomer), m.p. 247°-248° C.; tlc on silica gel in CHCl$_3$:MeOH (9:1 ) showed essentially a single spot, R$_f$=0.48. No polymer or other impurity was detected. L.C. assay showed 9-isomer=100.68%; 3-isomer, none detected. Overall yield=95.9%.

What is claimed is:

1. A process for purifying crude 9-(2,6-dihalobenzyl)-adenines, obtained by alkylating adenine, wherein the crude 9-(2,6-dihalobenzyl)adenines contain substantial amounts of 3-(2,6-dihalobenzyl)adenines which comprises transalkylating the 3-(2,6-dihalobenzyl)adenines in the presence of concentrated sulfuric acid and a carbenium ion trap selected from the group consisting of dialkyl sulfide, wherein the alkyl group contains 1 to 5 carbon atoms, diaryl sulfide, wherein the aryl groups contain 6 to 18 carbon atoms; benzene, toluene, xylene, mixed xylenes, mesitylene, alkoxybenzene wherein the alkyl group contains 1 to 3 carbon atoms; thiophene, iodobenzene, naphthalene and triphenylphosphine.

2. A process for reducing the concentration of 3-(2-chloro-6-fluorobenzyl)adenine in crude 9-(2-chloro-6-fluorobenzyl)adenine, obtained by alkylating adenine and containing substantial amounts of 3-(2-chloro-6-fluorobenzyl)adenine, to less than 100 ppm which comprises transalkylating the 3-(2-chloro-6-fluorobenzyl)adenine in the presence of concentrated sulfuric acid and toluene or mixed xylenes carbenium ion trap.

3. A process according to claim 2 wherein the transalkylation is carried out in the presence of excess concentrated sulfuric acid and toluene or mixed xylenes between room temperature and about 90° C. from 2 to 36 hours.

4. A process for reducing the concentration of 3-(2,6-dihalobenzyl)adenines in crude 9-(2,6-dihalobenzyl)adenines, obtained by alkylating adenine and containing substantial amounts of 3-(2,6-dihalobenzyl)adenines, to less than 100 ppm which comprises:
    (a) extracting the bulk of the 3-(2,6-dihalobenzyl)adenines with dilute mineral acid, and
    (b) transalkylating the remaining 3-(2,6-dihalobenzyl)adenines in the presence of concentrated sulfuric acid and a carbenium ion trap selected from the group consisting of dialkyl sulfide, wherein the alkyl group contains 1 to 5 carbon atoms; diaryl sulfide, wherein the aryl groups contain 6 to 18 carbon atoms; benzene, toluene, xylene, mixed xylenes, mesitylene, alkoxybenzene wherein the alkyl group contains 1 to 3 carbon atoms; thiophene, iodobenzene, naphthalene and triphenylphosphine.

5. A process according to claim 4 wherein said mineral acid is dilute nitric acid, hydrochloric acid or phosphoric acid.

6. A process for reducing the concentration of 3-(2-chloro-6-fluorobenzyl)adenine in crude 9-(2-chloro-6-fluorobenzyl)adenine, obtained by alkylating adenine and containing substantial amounts of 3-(2-chloro-6-fluorobenzyl)adenine, to less than 100 ppm which comprises:

(a) extracting the bulk of the 3-(2-chloro-6-fluorobenzyl)adenine with dilute nitric acid, and (b) transalkylating the remaining 3-(2-chloro-6-fluorobenzyl)adenine in the presence of concentrated sulfuric acid and toluene or mixed xylene carbenium ion trap.

7. A process for reducing the concentration of 3-(2-chloro-6-fluorobenzyl)adenine in crude 9-(2-chloro-6-fluorobenzyl)adenine, obtained by alkylating adenine and containing substantial amounts of 3-(2-chloro-6-fluorobenzyl)adenine, to less than 100 ppm which comprises:

(a) extracting the bulk of the 3-(2-chloro-6-fluorobenzyl)adenine with dilute nitric acid solution containing an approximately equimolar amount of acid with respect to 3-(2-chloro-6-fluorobenzyl)adenine wherein the extraction is carried out between room temperature and up to reflux temperature with rapid stirring, and (b) transalkylating the remaining 3-(2-chloro-6-fluorobenzyl)adenine in the presence of excess concentrated sulfuric acid and in the presence of excess toluene or mixed xylenes wherein the transalkylation is carried out between room temperature and about 90° C. from 2 to 36 hours.

* * * * *